Oct. 25, 1949. H. C. SWIM Plant Pat. 885
ROSE PLANT
Filed Oct. 14, 1947
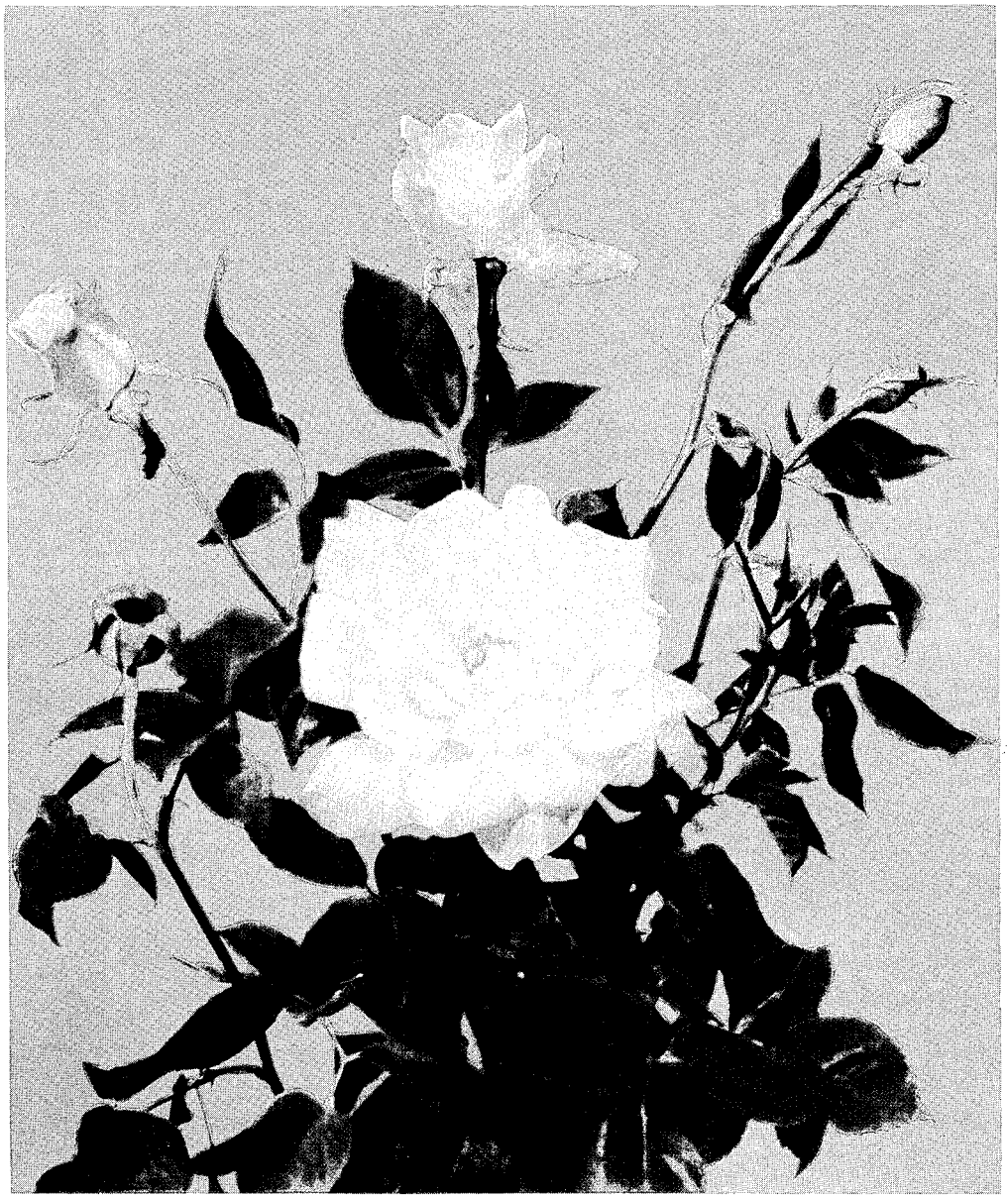
Inventor
H. C. Swim
By Robert Robb
attorneys Patented Oct. 25, 1949

Plant Pat. 885

UNITED STATES PATENT OFFICE

885

ROSE PLANT

Herbert C. Swim, Ontario, Calif., assignor to Armstrong Nurseries, Inc., Ontario, Calif., a corporation of California Application October 14, 1947, Serial No. 779,723

1 Claim. (Cl. 47—61)

The present invention relates to a new and distinct variety of rose plant, originating as a cross between the known varieties "Signora" (Pl. Pat. No. 201) and "Charlotte Armstrong" (Pl. Pat. No. 455).

This cross was made by me primarily for the purpose of obtaining recessive genetic factors for yellow color from both parents, with the hope of, at the same time, obtaining a re-grouping of the better characteristics of each parent in the offspring. These objectives have been accomplished in this new variety, hereinafter described, to a very satisfactory degree.

It will be apparent upon examination that this new variety of rose differs from either of its parents in the combination of its characteristics, although it resemblances one or the other of them in several.

The dominating and distinct characteristics of this combination are as follows:

(*a*) Plants are of very vigorous growth normally clothed with large, leathery, and glossy foliage which unlike most foliage of its type, has a high degree of resistance to both mildew and black spot.

(*b*) Long pointed to urn shaped buds opening to flowers with high centers at first, later becoming open, and with both buds and flowers in shades of color substantially described herein and to the best of my knowledge distinct from any colors heretofore known in varieties now in commerce.

(*c*) Flower stems characterized by their length, strength, and relative freedom from prickles especially small ones, and with a peduncle moderately thickly covered with small thorns and spines or prickles on all but the shorter, weaker flower stem.

(*d*) A penetrating tea-rose fragrance to the flowers.

(*e*) The tendency of the flowers to burn in hot weather just before the petals drop.

Asexual reproduction shows that the characteristics hold true through succeeding propagations.

In order to more specifically point out the distinctions from the individual parents, it may be noted that this new variety differs in the following respects:

(1) It has a much longer bud than its pollen parent "Signora," with a color much more predominantly in the shade popularly described as gold, or orange-yellow, and with the petals in the open flower more regularly arranged.

(2) A plant with growth habit intermediate that of the two parents, being neither as upright as "Signora" nor as spreading as "Charlotte Armstrong."

(3) It differs from "Charlotte Armstrong" in the color of the bud and open flower since its seed parent is popularly described by the color terms Blood Red to Cerise varying yellow on the base of the petals. The foliage of this variety is glossy, whereas "Charlotte Armstrong" is classed as not glossy. This new variety has fewer prickles, both large and small, than does "Charlotte Armstrong."

In the drawing are shown specimens of the plant foliage, both young and mature, and specimens of the flowers at their different stages of development.

The following is a detailed description of the new variety, all reference to color being in accordance with the R. F. Wilson's Horticultural Colour Chart, except where indicated to be in accordance with Ridgway's Color Standards and Nomenclature:

Type: Hardiness untested: tall; bush; outdoor; seedling; for outdoor-grown cut flowers and garden decoration.
Class: Hybrid tea.
Breeding: Seedling.
*Seed parent.*—"Charlotte Armstrong."
*Pollen parent.*—"Signora."
Propagation: Holds its distinguishing characteristics through succeeding propagations by budding, the only method tried so far.

*Flower*

Locality where grown: Ontario, California.
Flowers borne: Singly, sometimes two or three, to stem; on strong, long stems.
Quantity of bloom: Very free; outdoors.
Continuity: Continuous during growing season.
Fragrance: Penetrating tea.
Bud:
*Peduncle.*—Medium long; medium heavy; erect; usually rough; moderately thickly covered with gland-tipped cilia and prickles. *Color*—Absinthe Green, Plate XXXI (Ridgway).
*Before calyx breaks.*—*Size*—medium to large. *Form*—long, pointed; with foliaceous appendages, few gland-tipped cilia and bloom on the surface of the bud; with slender, much cut foliaceous parts extending beyond the tip of the bud equal to ¾ or more of its length on most buds.
*As calyx breaks.*—*Color*—Aureolin, Plate 3/1, page 3, at base, becoming shaded and washed with Vermilion, Plate 18/1, page 18.

*Sepals.—Inner surface*—with fine, woolly tomentum. When the margin of a sepal is not covered by an adjacent sepal, it has woolly tomentum and stipitate glands on both margins; but if margin is covered by adjacent sepals, margin has only woolly tomentum.

*As first petal opens.—Size*—large. *Form*—long, pointed to urn shape. *Color*—outside: Buttercup Yellow, Plate 5/1, page 5, at base, becoming shaded and washed with Mandarin Red, Plate 17/1, page 17; inside: Buttercup Yellow, Plate 5, page 5, at base, becoming washed with Nasturtium Orange, Plate 610, page 145, and pencilled and shaded with Vermilion, Plate 18/1, page 18.

*Opening.*—Opens up well.

Bloom: Size, when fully open—large; 4 inches to 5 inches.

*Petalage.*—Double to very double; 30 to 35 petals; arranged regularly; from 4 to 7 petaloids arranged irregularly.

*Form.*—Full, high center at first; becoming open; petals remaining at first loosely rolled outward; becoming later, at maturity, tightly rolled outward.

Petals: Thick; with inside and outside satiny.

*Shape.—Outside*—obovate; scalloped with two to three notches. Intermediate—obovate-cuneate; scalloped with one to two notches. *Inside*—obovate-cuneate; scalloped irregular with one notch.

*Color.*—Colors may be modified by being pencilled, shaded, washed or tinted with other colors.

This description of a newly opened flower was made from a rose grown outdoors in the month of October, at Ontario, California:

*Color.—Outside petal*—outside surface: base of petal Lemon Yellow, Plate 4/1, page 4, shading to Lemon Yellow, Plate 4/3, page 4, pencilled and washed with Mandarin Red, Plate 17/2, page 17, to Mandarin Red, Plate 17/3, page 17; inside surface: base of petal Lemon Yellow, Plate 4, page 4, shading to Lemon Yellow, Plate 4/2, page 4, pencilled with Mandarin Red, Plate 17/2, page 17, and washed with Mandarin Red, Plate 17/3, page 17. *Intermediate petal*—outside surface: base of petal Lemon Yellow, Plate 4/1, page 4, shading to Lemon Yellow, Plate 4/3, page 4, washer near margin with Mandarin Red, Plate 17/3, page 17; inside surface: base of petal Lemon Yellow, Plate 4, page 4, shading to Lemon Yellow, plate 4/3, page 4, with slight pencilling near upper margin of Mandarin Red, Plate 17/3, page 17. *Inner petal*—outside surface: base of petal Lemon Yellow, Plate 4/1, page 4, shading to Lemon Yellow, Plate 4/3, page 4, washed near margin with Mandarin Red, Plate 17/3, page 17; inside surface: base of petal Lemon Yellow, Plate 4, page 4, shading to Lemon Yellow, Plate 4/3, page 4, with slight pencilling near upper margin of Mandarin Red, Plate 17/3, page 17.

This description was made from a rose that was open for three days outdoors in the month of October, at Ontario, California:

*Color. — Outside petal* — outside surface: small spot of Lemon Yellow, Plate 4/1, page 4, at base, with markings at lower margins of Spanish Orange, Plate 010/1, page 103, shading to Saffron Yellow, Plate 7/3, page 7, at upper margins, washed with Crimson, Plate 22/3, page 22, marked and pencilled with Crimson, Plate 22/2, page 22, and Scarlet, Plate 19/2, page 19; inside surface: base of petal Lemon Yellow, Plate 4/1, page 4, shading to Lemon Yellow, Plate 4/3, page 4, at upper margin, petal washed with Orange, Plate 12/2, page 12, and Vermilion, Plate 18/2, page 18, with pencilling of Geranium Lake, Plate 20/1, page 20, and Crimson, Plate 22/1, page 22. *Inside petal*—outside surface base of petal Lemon Yellow, Plate 4/1, page 4, shading through Lemon Yellow, Plate 4/2, page 4, to Lemon Yellow, Plate 4/3, page 4, washed with Orange, Plate 12/3, page 12; inside surface: base of petal Lemon Yellow, Plate 4, page 4, shading to Lemon Yellow, Plate 4/3, page 4, washed with Orange, Plate 12/3, page 12, pencilled with Mandarin Red, Plate 17/2, page 17.

*General color effect.—Newly opened flower*—near Chinese Yellow, Plate 606/1, page 68. *Three days open*—near Apricot, Plate 609/2, page 70.

*Behavior.*—Persist during hot weather till petals have begun to dry, fading yellow; affected by hot weather as follows: not as highly colored with reddish tints, and some burning results as flower finishes.

*Flower longevity.*—On bush in garden, four days in October. Cut roses grown outdoors kept at living room temperatures, three to four days in October. Untried for greenhouse growing.

*Reproductive organs*

Stamens: Medium number; arranged irregularly about pistils.

Filaments: Long; 6–15 mm. long; most with anthers. *Color*—Lemon Yellow, Plate 4, page 4, shading to Lemon Yellow, Plate 4/2, page 4, at upper end.

Anthers: Medium size; all open at once. *Color*—Canary Yellow, Plate 2/2, page 2.

Pollen: Color, near Yellow Ochre, Plate 07, page 101.

Pistils: Medium number; 35–40 in number.

Styles: Uneven; thin; loosely bunched; 6–9 mm. long. *Color*—Rose Red, Plate 724, page 158, shading at base to near Uranium Green, Plate 63/2, page 63.

Stigma: Color, near Lemon Yellow 4/3, page 4, translucent.

Ovaries: Usually all enclosed in calyx.

Hips: Globular, with inconspicuous neck. *Color*—near Olive Yellow, Plate XXX (Ridgway) shaded on one side varying from Light Cadmium, Plate IV (Ridgway) to Peach Red, Plate I (Ridgway). Moderately smooth; walls thick and fleshy.

Sepals: Permanent; moderately long; recurved. *Color*—inside: near Snuff Brown, Plate XXIX (Ridgway); outside: near Sayal Brown, Plate XXIX (Ridgway).

Seeds: Few; large; three to eight in number.

*Plant*

Foliage:

*Leaves.*—Compound of usually five leaflets; normal quantity; large; heavy to leathery and glossy.

*Leaflets.—Shape*—oval with apex mucronate; base round; margin doubly serrate.

*Color.—Mature*—upper surface: near Dark Yellow-Green, Plate XXXII (Ridgway). Midrib of near Glass Green, Plate XXXI (Ridgway); under surface: near Asphodel Green, Plate XLI (Ridgway), midrib near Glass Green, Plate XXXI (Ridgway). *Young*—upper surface: Courge Green, Plate XVII (Ridgway), midribs, veins, and margins of Brick Red, Plate XIII (Ridgway); under surface: Kildare Green, Plate XXXI (Ridgway), washed with near Etruscan Red, Plate XXVII (Ridgway).

*Rachis.—Heavy*—upper side: grooved, with few stipitate glands on edges; under side: sparsely hairy.

*Stipules.*—Long; medium width; with medium points recurved toward the stem.

*Disease.*—More than average resistant to mildew and blackspot.

Growth:

*Habit.*—Bushy; upright; much branched.

*Growth.*—Very vigorous.

*Canes.*—Heavy.

*Main Stems.*—Light Cress Green, Plate XXXI Ridgway). *Large prickles*—several; long; hooked downward; with long, broad base. *Color*—near Chestnut, Plate III (Ridgway).

*Small prickles and hairs*—none.

*Branches.*—Near Rainette Green, Plate XXXI (Ridgway). *Large prickles*—few; medium length; hooked downward; with long, narrow base. *Color*—near Chestnut, Plate II (Ridgway). *Small prickles and hairs*—none.

*New shoots.*—Near Absinthe Green, Plate XXXI (Ridgway). *Large prickles*—very few; medium length; hooked downward; with long, narrow base. *Color*—near Chrysolite Green, Plate XXXI (Ridgway), shading to Terra Cotta, Plate XXVIII (Ridgway), at base. *Small prickles and hairs*—none.

I claim:

A new and distinct variety of rose plant, characterized as to novelty by vigorous growth and production of large, leathery, and glossy foliage; high degree of resistance to mildew and blackspot; the form of the buds and flowers and their coloring in the respective stages of development; the long, strong flower stems and their relative freedom from prickles; and the penetrating tea-rose fragrance of the flowers, substantially as shown and described.

HERBERT C. SWIM.

No references cited.